US00PP22311P2

(12) United States Plant Patent
Smith et al.

(10) Patent No.: US PP22,311 P2
(45) Date of Patent: Dec. 6, 2011

(54) *MISCANTHUS* PLANT NAMED 'GOLD BREEZE'

(50) Latin Name: *Miscanthus sinensis*
Varietal Denomination: Gold Breeze

(76) Inventors: Michael Vern Smith, Scappoose, OR (US); Maurice R. Horn, Portland, OR (US); Scott Christy, Warren, OR (US)

( * ) Notice: Subject to any disclaimer, the term of this patent is extended or adjusted under 35 U.S.C. 154(b) by 114 days.

(21) Appl. No.: 12/657,745

(22) Filed: Jan. 27, 2010

(51) Int. Cl.
*A01H 5/00* (2006.01)

(52) U.S. Cl. ..... Plt./384

(58) Field of Classification Search ..... Plt./384
See application file for complete search history.

(56) References Cited

U.S. PATENT DOCUMENTS

PP15,193 P2 * 9/2004 Smith et al. ..... Plt./384
PP16,179 P3 * 1/2006 Zaiger et al. ..... Plt./197

OTHER PUBLICATIONS

Anonymous. "Emerald Coast Debuts Miscanthus 'Gold Breeze'" Greenhouse Grower. Nov. 18, 2009. available at: http://www.greenhousegrower.com/news/?storyid=2799.*
Anonymous. GardenWeb Glossary of Botanical Terms results for "palea". Accessed Jul. 14, 2011. Available at: http://glossary.gardenweb.com.*

* cited by examiner

*Primary Examiner* — Wendy C Haas
(74) *Attorney, Agent, or Firm* — Penny J. Aguirre

(57) ABSTRACT

A new cultivar of *Miscanthus, Miscanthus sinensis* 'Gold Breeze', that is characterized by its stiff leaf blades that are densely banded with alternating bands of creamy yellow and apple green with the banding consistent from the base to the tip of the leaf blade, its moderate plant height, its upright plant habit with foliage that is dense and bushy and resists lodging, and its late season bloom of bright purple-red inflorescences in late September to early October in Oregon.

3 Drawing Sheets

Botanical classification: *Miscanthus sinensis.*
Cultivar designation: 'Gold Breeze'.

BACKGROUND OF THE INVENTION

The present invention relates to a new and distinct cultivar of *Miscanthus sinensis* and will be referred to hereafter by its cultivar name, 'Gold Breeze'. 'Gold Breeze' represents a new cultivar of Japanese silver grass, a cold hardy, perennial ornamental grass grown for landscape use.

The Inventors discovered the new cultivar as a chance seedling in a field planted with stock plants of *Miscanthus sinensis* 'Strictus' (not patented) at their nursery in Scappoose, Oreg. in summer of 1996. The Inventors evaluated 'Gold Breeze' along side other chance seedlings for a period of 10 years before selecting 'Gold Breeze' as a single unique plant of *Miscanthus. Miscanthus sinensis* 'Strictus' (not patented) is considered by the Inventors to be a likely seed parent based on the characteristics of 'Gold Breeze' and its close proximity in the field plot.

Asexual reproduction of the new cultivar was first accomplished by culm division in Scappoose, Oreg. in late winter of 2007 by the Inventors. The characteristics of this cultivar have been determined to be stable and are reproduced true to type in successive generations.

SUMMARY OF THE INVENTION

The following traits have been repeatedly observed and represent the characteristics of the new cultivar after observation for a period of twelve years in Scappoose, Oreg. These attributes in combination distinguish 'Gold Breeze' from all other cultivars of *Miscanthus* known to the Inventors.

1. 'Gold Breeze' exhibits leaf blades that are densely banded with alternating bands of creamy yellow and apple green with the banding consistent from the base to the tip of the leaf blade.
2. 'Gold Breeze' exhibits a moderate plant height; reaching a height of up to 1.8 m (6 feet).
3. 'Gold Breeze' exhibits an upright plant habit with foliage that is dense and bushy and resists lodging.
4. 'Gold Breeze' exhibits leaf blades that are stiff throughout the length of the leaf with only the tips arching downward.
5. 'Gold Breeze' blooms in late September to early October in the Northwest with inflorescences that open purple-red and turn tawny brown as they mature.

'Gold Breeze' differs from its probable seed parent plant, 'Strictus', in having a denser banding habit, in being shorter in height, in flowering later in the season and in having a denser and more bushy growth habit. 'Gold Breeze' can be most closely compared to the cultivars 'Kirk Alexander' (not patented) and 'Zebrinus' (not patented). 'Gold Breeze' differs from 'Kirk Alexander' in having leaf blades with a more dense and even banding pattern, a more dense, bushy and upright growth habit, a tighter more dense plant base, and in having inflorescences that are a brighter red in color. 'Gold Breeze' differs from 'Zebrinus' in being more upright and bushy, in maturing to a shorter height, in having leaf banding that is distributed from the base of the blade to the leaf tip, and in having leaf blades that narrower in width.

BRIEF DESCRIPTION OF THE DRAWING

The accompanying colored photographs illustrate the overall appearance and distinct characteristics of the new *Mis-*

*canthus*. The photographs were taken in October of plants 12 years in age as grown outdoors in Scappoose, Oreg.

Figure 1:
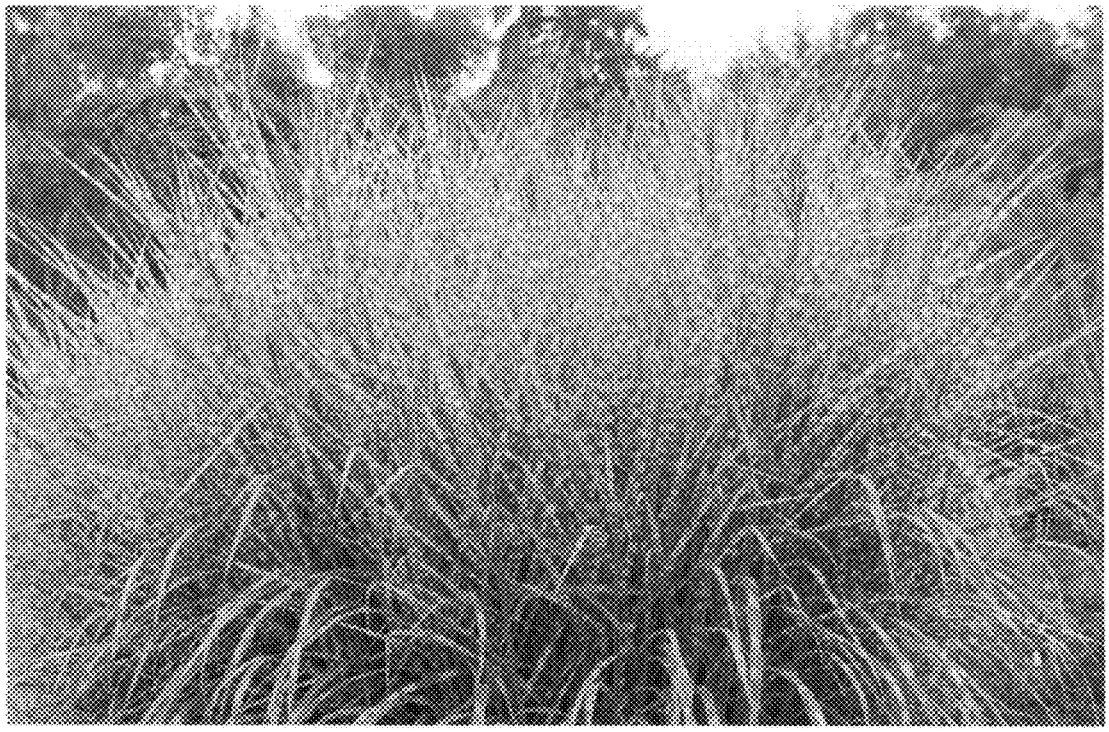

The photograph in FIG. 1. provides a side view of a plant of 'Gold Breeze' and illustrates the overall plant habit and general appearance.

Figure 2:
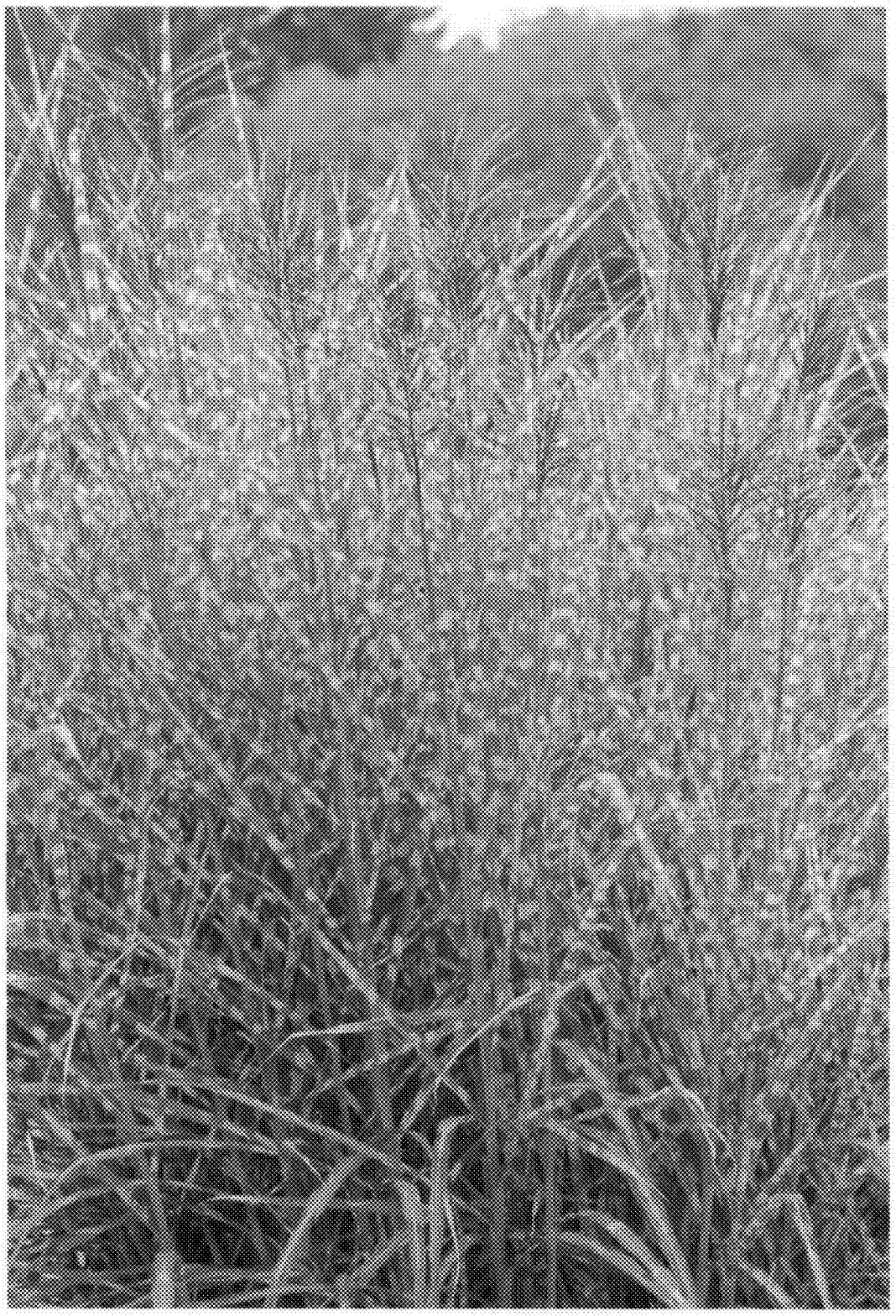

The photograph in FIG. 2. provides a close-up view of the banding pattern of the leaf blades of Gold Breeze.

Figure 3:
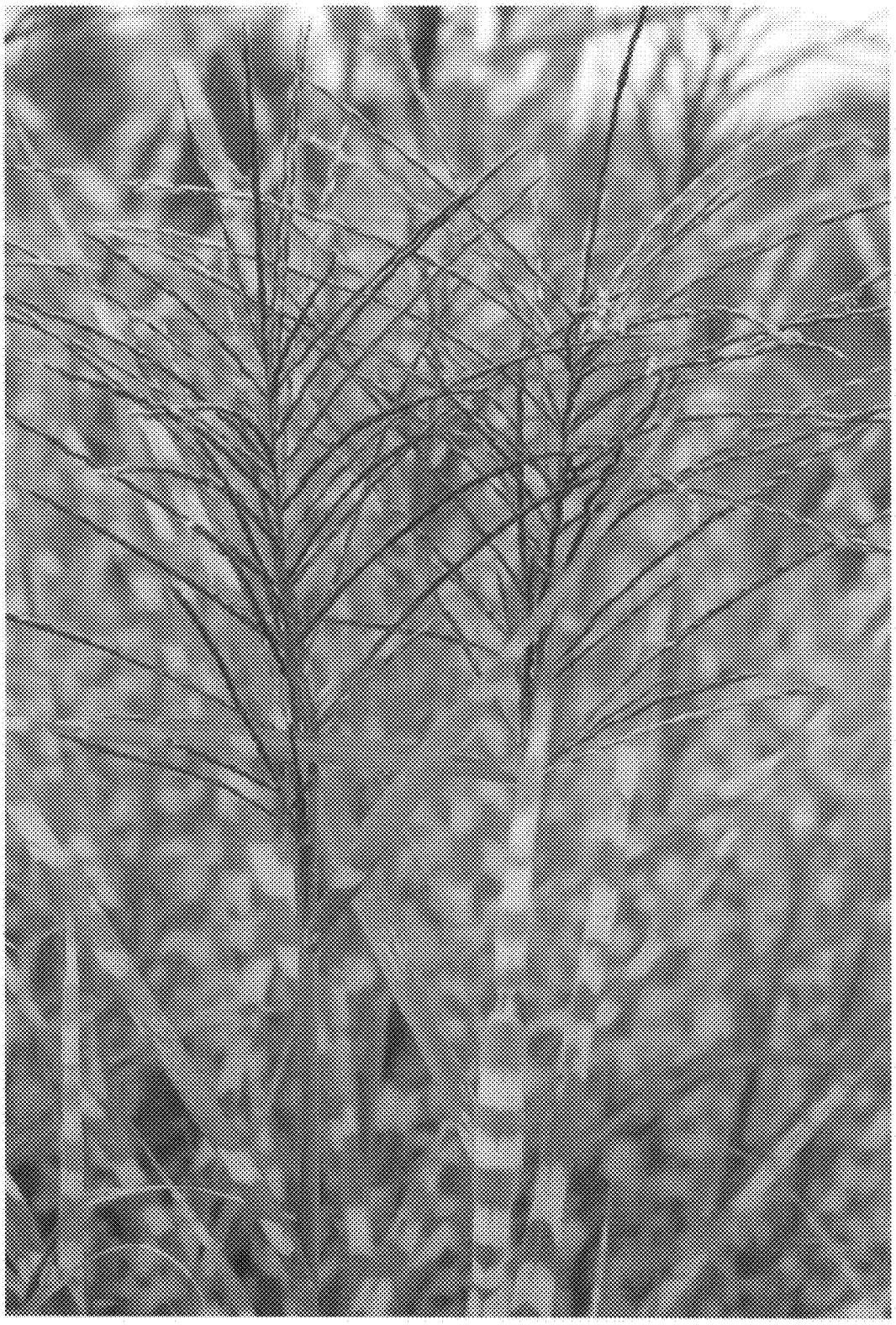

The photograph in FIG. 3. provides a close-up view of two inflorescences of Gold Breeze. The colors in the photographs may differ slightly from the color values cited in the detailed botanical description, which accurately describe the colors of the new *Miscanthus*.

DETAILED BOTANICAL DESCRIPTION

The following is a detailed description of the new cultivar as grown in an outdoor trial bed for twelve years in Scappoose, Oreg. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Botanical classification: 'Gold Breeze' is a cultivar of *Miscanthus sinensis*.

Parentage: Naturally occurring seedling of *Miscanthus sinensis* 'Strictus'.

General description:

- *Blooming period.*—Blooms in late September to early October in the Northwest U.S. blooms are retained over the winter.
- *Plant habit.*—Herbaceous, clump-forming, ornamental grass with an upright, rigid form and dense, bushy foliage.
- *Height and spread.*—Reaches up to 1.8 m (6 feet) in height with a spread of about 30 to 35 cm (12 to 14 inches) at base for a plant 3 years in age.
- *Hardiness.*—U.S.D.A. Zones 5 to 9.
- *Culture.*—Grows best in fertile, moist soil in full sun, tolerates wet soils and light shade in climates with high temperatures.
- *Diseases and pests.*—No susceptibility or resistance to diseases or pests has been observed.
- *Root description.*—Fibrous.

Growth and propagation:

- *Propagation.*—Culm division, tissue culture is also possible.
- *Growth rate.*—Moderate.

Culm (stem) description:

- *General.*—Cylindrical, flattened, completely enclosed by leaf sheaths in a fan-like arrangement.
- *Culm aspect.*—Rigid and held erect.
- *Culm color.*—A blend of 138A and 138B.
- *Culm size.*—An average of 6 mm in width, an average of 1.2 m in height on mature plants.
- *Culm surface.*—Glabrous, dull and finely ridged.
- *Ligule.*—Membranous becoming papery, about 1 to 3 mm width and 161A in color with fine white hairs on inner surface about 3 mm in length and 161A in color, encircles the entire leaf junction but glabrous on outer surface of leaves.

Foliage description:

- *Leaf shape.*—Linear.
- *Leaf division.*—Simple.
- *Leaf base.*—Sheathed.
- *Leaf apex.*—Acute, tapering to a fine point.
- *Leaf aspect.*—Emerging leaves are erect, leaf blades diverge from leaf sheath at ligule at up to a 30° to 45° angle outward from culm, blades are concave, stiff and curve downward at tips when mature.
- *Leaf venation.*—Parallel, mid rib is raised on upper surface but not conspicuous, color matches the color of the leaf blades on inner and outer surface.
- *Leaf margins.*—Entire, with sharp short bristles that are not visually noticeable.
- *Internode length.*—An average of 6.5 cm.
- *Leaf persistence.*—Foliage dries but is persistent throughout the winter.
- *Leaf attachment.*—Sheathed, leaf is sheathed from the base of culm and the blade extends out from the culm at a ligule.
- *Leaf size.*—An average of 45 cm in length, an average of 8.5 mm in width tapering to a point at the apex.
- *Leaf surface.*—Glabrous on upper and slightly glaucous on lower surface.
- *Leaf number.*—An average of 11 on a culm 90 cm in length.
- *Leaf arrangement.*—Alternate, 2 ranked.
- *Leaf color and banding description.*—Banding is composed of alternating green and creamy yellow bands on the upper and lower surface of the leaf blades, an average of 14 yellow bands and 14 green bands per leaf blade measuring 44 cm in length, bands extend the entire width of the leaf blade with bands an average of 1.5 cm in length, yellow bands are 11A in color on upper and lower surface and green bands are a color between 147A and 137A on upper surface and 137A on lower surface.

Flower description:

- *General description.*—Compact, fan-shaped panicle terminating from each culm in late September to early October in Oregon, composed of numerous slender, silky aggregate racemes, cascading to one side, spikelets arranged in pairs on individual zig-zag like racemes.
- *Lastingness of inflorescence.*—Panicles are persistent from fall through winter.
- *Fragrance.*—None.
- *Panicle color.*—Emerges a blend between 145B and 145C and becoming heavily diffused with 187A and 187B and changes to about 161A during plant dormancy.
- *Panicle size.*—An average of 22 cm in length and 9 cm in width with individual racemes an average of 10 cm in length and 3 cm in width.
- *Peduncle.*—An average of 10 cm in length and 0.5 mm in width, glabrous surface and 147A in color.
- *Pedicels.*—Unequal in length on pairs of spikelets, an average of 4 mm in length and 0.5 m in width and 147A in color.
- *Spikelet description.*—Equal membranous glumes about 4 mm in length and 1 mm in width and a blend of 151A and 200A in color, shorter hyaline lemma extending into very fine, flexuous fine awn extending about 8 mm beyond spikelet, palea small and hyaline.
- *Spikelet size.*—About 5 mm in length and 2 mm in width (excluding awn).

*Spikelet hairs.*—Emerging from the base as a tuft surrounding the base, long, average of 3.5 mm in length, very fine, about N77B in color and changing to about 155B in color.

Reproductive organs:

*Androecium.*—Anthers; 3, 3 mm in length and 0.8 mm in width, 200C in color, basifixed on very fine filament extending about 1.5 mm from spikelet, pollen; not visible.

*Gynoecium.*—Pistil; 1, 2 plumose stigmas on short, file styles, stigma color is 202A, 1.5 mm in length and 0.3 mm in width, ovary; 1-locular, superior, minute, not easily quantifiable in size and color.

*Caryopsis.*—No caryopsis production was observed.

It is claimed:

1. A new and distinct cultivar of *Miscanthus* plant named 'Gold Breeze' as herein illustrated and described.

* * * * *